United States Patent [19]

Lundsgaard et al.

[11] Patent Number: 5,525,518
[45] Date of Patent: Jun. 11, 1996

[54] METHOD OF PHOTOMETRIC IN VITRO DETERMINATION OF A BLOOD GAS PARAMETER IN A BLOOD SAMPLE

[75] Inventors: Finn C. Lundsgaard, Tastrup; Niels-Henrik Jensen, Farum; Willy Andersen, Espergærde, all of Denmark

[73] Assignee: Radiometer Medical A/S, Bronshoj, Denmark

[21] Appl. No.: 720,530

[22] PCT Filed: Dec. 21, 1989

[86] PCT No.: PCT/DK89/00302

§ 371 Date: Jun. 21, 1991

§ 102(e) Date: Jun. 21, 1991

[87] PCT Pub. No.: WO90/07106

PCT Pub. Date: Jun. 28, 1990

[30] Foreign Application Priority Data

Dec. 22, 1988 [DK] Denmark .................................. 7162/88

[51] Int. Cl.$^6$ .......................... G01N 33/50; G01N 33/48
[52] U.S. Cl. .......................... 436/68; 436/164; 436/165; 422/82.05; 422/82.09; 356/39; 356/434; 128/633
[58] Field of Search ............................ 436/66, 68, 164, 436/165; 422/58, 82.05, 82.06, 82.09, 102; 356/39, 40, 246, 434; 604/198, 263, 411; 128/633

[56] References Cited

U.S. PATENT DOCUMENTS

| | | | |
|---|---|---|---|
| 3,926,521 | 12/1975 | Ginzel | 356/39 |
| 4,339,317 | 7/1982 | Meiattini et al. | 204/400 |
| 4,420,254 | 12/1983 | Smeaton | 356/246 |
| 4,426,451 | 1/1984 | Columbus | 436/518 |
| 4,444,498 | 4/1984 | Heinemann | 128/633 X |
| 4,447,150 | 5/1984 | Heinemann | 356/41 |
| 4,454,229 | 6/1984 | Zander | 436/68 |
| 4,496,344 | 1/1985 | Kamstra | 604/191 X |
| 4,509,522 | 4/1985 | Manuccia et al. | 128/634 |
| 4,645,744 | 2/1987 | Charlton | 436/74 |
| 4,654,197 | 3/1987 | Lilja | 422/56 |
| 4,657,736 | 4/1987 | Marsoner et al. | 422/56 |
| 4,675,019 | 6/1987 | Bellhouse et al. | 604/408 |
| 4,703,182 | 10/1987 | Kroneis et al. | 250/458.1 |
| 4,737,144 | 4/1988 | Choksi | 604/198 |
| 4,745,279 | 5/1988 | Karkar et al. | 356/40 X |
| 4,775,514 | 10/1988 | Barnikol et al. | 422/55 X |
| 4,781,701 | 11/1988 | Geprägs | 604/240 |
| 4,810,090 | 3/1989 | Boucher et al. | 356/73 X |
| 4,873,993 | 10/1989 | Meserol | 128/760 |
| 4,929,426 | 5/1990 | Bodai | 422/63 |
| 4,940,945 | 7/1990 | Littlejohn | 324/438 |
| 4,997,769 | 3/1991 | Lundsgaard | 436/67 X |
| 5,025,798 | 6/1991 | Schindele | 128/771 |
| 5,029,583 | 7/1991 | Meserol et al. | 128/633 |
| 5,046,496 | 9/1991 | Betts | 128/635 |
| 5,064,618 | 11/1991 | Baker | 422/82.01 |
| 5,066,859 | 11/1991 | Karker | 250/339.09 |
| 5,080,865 | 1/1992 | Leiner | 422/68.1 |
| 5,120,510 | 6/1992 | Gourley et al. | 422/82.07 |
| 5,127,077 | 6/1992 | Iyer et al. | 385/116 |

FOREIGN PATENT DOCUMENTS 0185126  6/1986  European Pat. Off. .

*Primary Examiner*—James C. Housel
*Assistant Examiner*—Maureen M. Wallenhorst
*Attorney, Agent, or Firm*—Bryan Cave

[57] ABSTRACT

A method of photometric in vitro determination of at least one blood gas parameter in a sample of whole blood. The whole blood sample is obtained by connecting an at least partially transparent sample container to an in vivo locality and transferring whole blood into the sample container, then breaking the connection. The sample container is arranged in an optical system which has a radiation source and a means for detecting radiation to locate the sample container between the radiation source and the radiation detection means. Radiation is transmitted to the sample from the radiation source and radiation emitted from the sample is transmitted to the radiation detection means. The detected radiation is used to determine the blood gas parameter of the sample. A system for use in this method has a radiation source, a radiation detection means, an at least partially transparent sample container, and a sample container station.

2 Claims, 11 Drawing Sheets

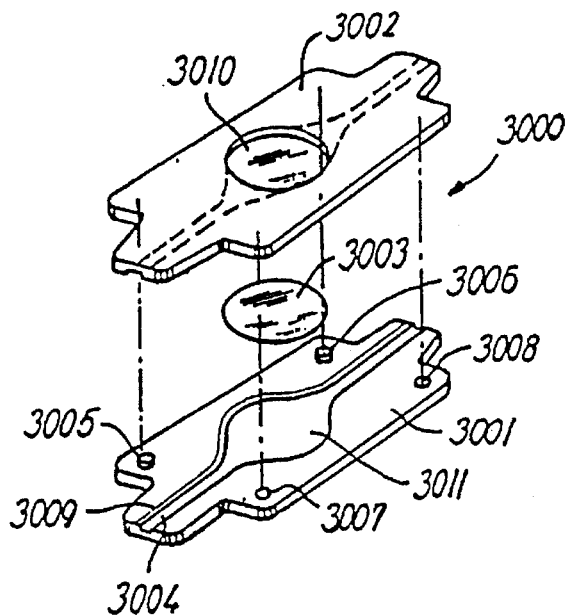
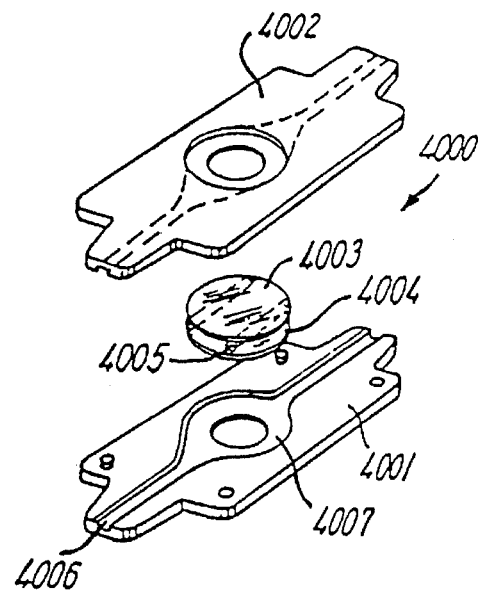
FIG. 11    FIG. 12
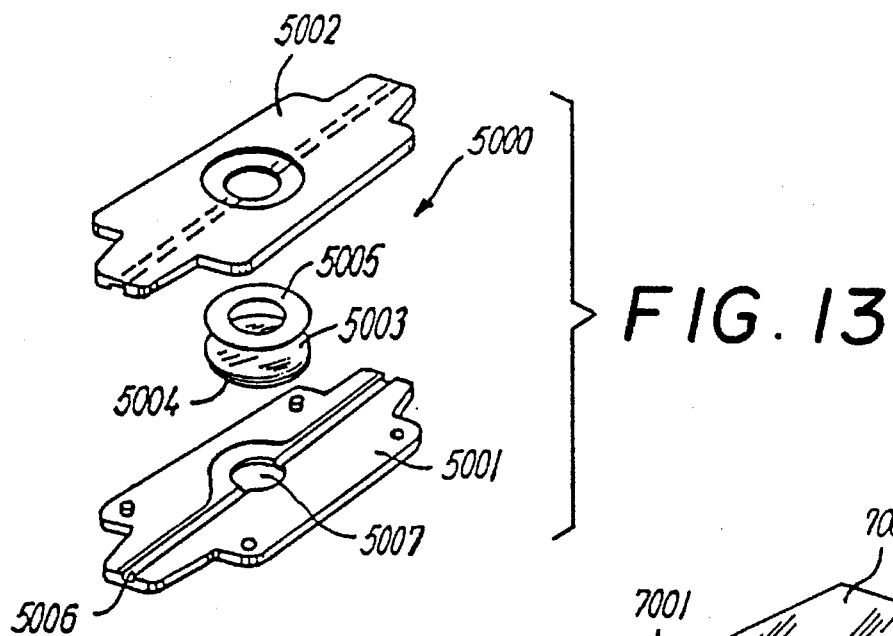
FIG. 13
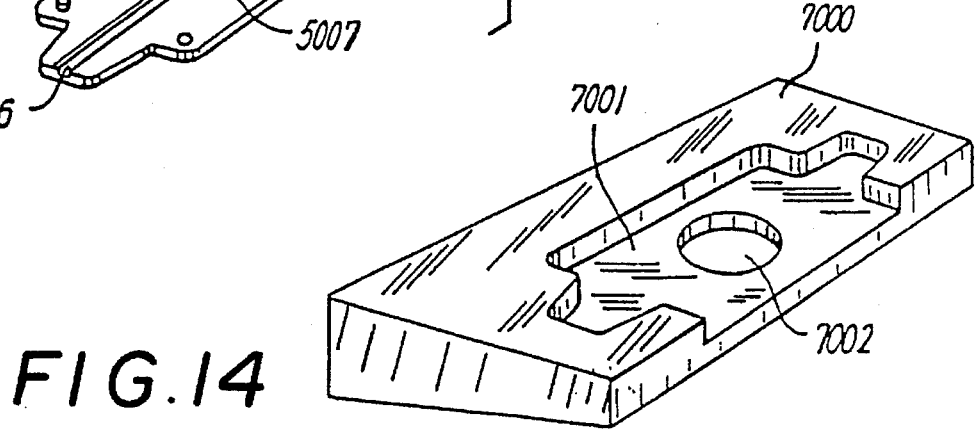
FIG. 14

METHOD OF PHOTOMETRIC IN VITRO DETERMINATION OF A BLOOD GAS PARAMETER IN A BLOOD SAMPLE

FIELD OF INVENTION

The present invention relates to a method of photometric in vitro determination of a blood gas parameter in a blood sample.

BACKGROUND OF THE INVENTION

Photometric analysis of the blood gas parameters pH, oxygen ($O_2$) and carbon dioxide ($CO_2$) is in itself prior art, which is described in detail in a large number of publications. A representative selection of these publications is listed below.

Photometric determination of the oxygen concentration in blood or other media by the so-called luminescence quenching is thus known from i.e., Bacon, J. R. and Demas, J. N., "Determination of oxygen concentrations by luminescence quenching of a polymer immobilized transition-metal complex", Anal. Chem., 59, 1987, 2780–2785, Longmuir, I. S. and Knopp, J. A., "Measurement of tissue oxygen with a fluorescent probe", Journal of applied physiology, 41, 1976, 598–602, Waughan, W. M. and Weber, G., "Oxygen quenching of pyrenebutyric acid fluorescence in water. A dynamic probe of the microenvironment", Biochemistry, 9 (3), 1970, 464–473, Bergman, I., Nature 218, 1958, 376, Stevens in the specification of U.S. Pat. No. 3,612,866, Stanley in the specification of U.S. Pat. No. 3,725,658, Bacon, J. R. and Demas, J. N. in the specification of British patent application GB 2132348, Peterson et al. in the specification of U.S. Pat. No. 4,476,870, Buckles, R. G. in the specification of U.S. Pat. No. 4,399,099, Hirschfeld, T. in the specification of U.S. Pat. No. 4,542,987, Dukes et al., in the specification of U.S. Pat. No. 4,716,363, Lübbers et al. in the specification of U.S. Pat. No. Re. 31,879, Kahil et al. in the specification of International patent application WO 87/0023, Murray, R. C., Jr. and Lefkowitz, S. M. in the specification of European patent application EP 190829, Murray, R. C., Jr. and Lefkowitz, S. M. in the specification of European patent application EP 190830, and Hesse, H. C. in the specification of East German patent DD 106086.

Determination of the carbon dioxide content in blood by irradiating with 4,26 μm radiation is known from:

Manuccia et al. in the specification of U.S. Pat. No. 4,509,522,

Mosse, C. A. and Hillson, P. J. in the specification of British patent application GB 2160646, and Nestor, J. R. in the specification of European patent application EP 253559.

Determination of pH in blood by contact with a pH indicator is known from, i.e., the following publications:

Seitz, W. R. and Zhujun, Z. in the specification of U.S. Pat. No. 4,548,907,

Wolfbeis, O. S. et al., "Fluorimetric analysis. 1. A study of fluorescent indicators for measuring near neutral ("physiological") pH-values", Fresenius Z. Anal. Chem. 1983, 314, 119–124, Peterson, J. I. et al., "Fiber optic pH probe for physiological use", Anal. Chem. 1980, 52, 864–869, Kirkbright, G. F. et al., "Fiber optic pH probe based on the use of an immobilized colorimetric indicator", Analyst 109, 1984, 1025–1026, and Gerich I. L. et al., "Optical fluorescence and its application to an intravascular blood gas monitoring system", IEEE Transactions on Biomedical Engineering 2, 1986, 117–132.

Determination of the intraarterial values of all three blood gas parameters by means of a fluorescence based measuring system is known from Miller et al,. "Performance of an in-vivo, continuous blood-gas monitor with disposable probe", Clin. Chem. 33 (9), 1987, 1538–1542. Extracorporeal determination of all three parameters by means of an also fluorescence based measuring system Gas-STAT™, produced by Cardiovascular Devices Inc., USA, is finally described in brochures concerning this system and in the article by Clark, C. L., "Early clinical experience with Gas-STAT", J. Extracorporeal Technol., 18 (3), 1986, 185–189. The determination of the blood gas parameters proceeds continuously in the Gas-STAT™ system. Inside a cuvette, which is inserted in the extracorporeal circulation established at a cardiac operation, fluorescence based sensors are placed. Via optical fibers excitation radiation is provided and emitted fluorescence radiation is taken away. The intensity of the latter depends of the concentration of the matter measured by the relevant sensor.

None of these publications relating to photometric analysis of the blood gas parameters describes an in vitro method for determination of one or several blood gas parameters in discrete samples and based on simple sample handling principles.

However, in vitro determination of the blood gas parameters pH, oxygen, and carbon dioxide in a blood sample has so far mostly been performed by means of blood gas analyzers as, e.g. the blood gas analyzers produced and sold by Radiometer A/S, Copenhagen, under the name ABL Acid-Base Laboratory.

These analyzers are mechanically complex, since the blood samples i.a. have to pass through the very fine fluid conduits of the analyzer, in which conduits electrochemical sensors are built-in. Blockage in the conduits or coatings on the active surfaces of the sensors can easily occur and interfere in or destroy a measurement.

On account of these circumstances the existing equipment requires frequent maintainance performed by specially trained personnel, and the equipment will normally be placed in a laboratory situated at a certain distance from the patient. A period of reply of more than 10 min. and normally up to half an hour from the time of the sampling to the moment of the analysis result being present is therefore not unusual. Beyond that the waiting period can be unfortunate in connection with the medical treatment of the patient, the relatively long waiting period also has the consequence that the sample is to be kept cooled down to app. 0° C. This is due to the fact that at higher temperatures the metabolic processes of the blood will cause changes in the blood gas parameters during the relevant periods.

Another disadvantage of the existing equipment is that there exists a certain risk for the operator to get in touch with sample residue with the health risks this may imply in the form of transfer of infections, etc.

SUMMARY OF THE INVENTION

The object of the invention is to provide an in vitro method for determination of a blood gas parameter, the method being more appropriate for the user in that there is obtained both a more simple and less risky sample handling and a more simple maintenance of the analyzer.

The method according to the invention is characterized in that the blood sample is transferred directly from an in vivo locality to an at least partially transparent sample container, that the connection between the sample containing sample container and the blood circulation is broken, that subsequently the sample container with its content of blood sample is brought into optical communication with an optical system adapted to the relevant blood gas parameter and comprising a radiation source and a radiation detector interacting therewith, and that the blood gas parameter is determined on the basis of the radiation detected by the radiation detector.

In a preferred embodiment the method is characterized in, that the optical communication is provided by placing the sample container in a sample container station in an analyzer.

Alternatively, the optical communication can be established by one or several cables, which via contact elements to the sample container and optical fibres establish optical communication between the optical system and the sample container.

BRIEF DESCRIPTION OF THE DRAWINGS

FIG. 11 is a perspective view of a sample container for use in determining pH;

FIG. 12 is a perspective view of a sample container for use in determining $CO_2$ or hemoglobin;

FIG. 13 is a perspective view of a sample container for use in determining $O_2$;

FIG. 14 is a perspective view of a holder for the sample container shown in FIG. 12;

In the different figures like reference numerals designate like parts.

DETAILED DESCRIPTION OF THE INVENTION

Figure 1:
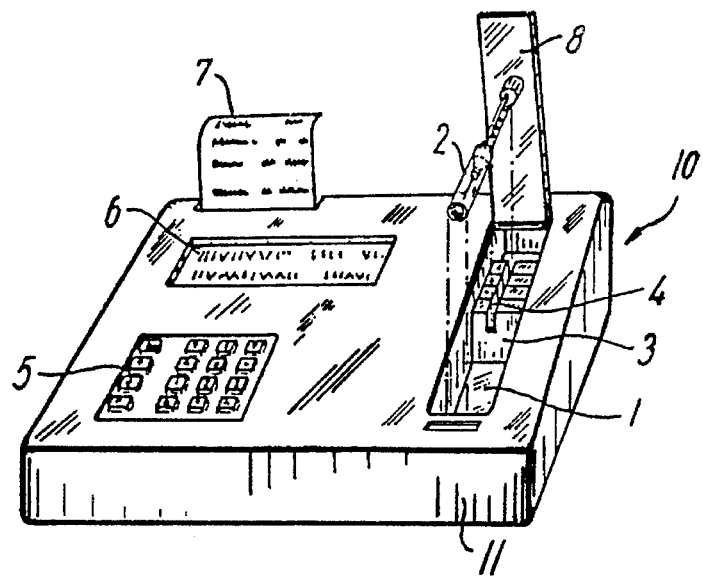
FIG. 1 is a perspective view of the preferred embodiment of an analyzer and a sample container, which together constitute the system according to the invention for photometric in vitro determination of a blood gas parameter in a blood sample.

The above mentioned less risky sample handling is i.a. a consequence of the possibility of removing the practically closed sample container with its content of blood sample after the termination of the analysis procedure. This removal is a sanitarily appropriate arrangement, which—in relation to the methods, by which a sample is transferred from the sampling container to an analyzer and from there to a waste container—reduces the risk for the user to get in touch with possibly infected sample residues.

The actual transfer of the blood sample from the sampling device to the measuring apparatus according to the prior art is a not unessential source of error within blood gas analysis. This source of error is eliminated by the method according to the present invention.

Apart from the more simple and less risky sample handling and the reduced maintenance of the analyzer obtained by the method according to the present invention, there is also in other ways obtained a simplified analysis procedure compared to the current blood gas analysis methodology.

The current methodology using equipment based on electrochemical sensors normally involves a relatively frequent calibration of the sensors. By traditional blood gas analyzers calibration routines are prescribed, whereby the sensors with an interval of 1 to 2 hours are contacted by a liquid or gaseous calibration medium with a specific content of the relevant parameters. The calibration medium is discarded after use and the operator therefore has to secure the presence of the necessary calibration medium. By the realization of the method according to the invention this calibration medium consuming calibration process can be avoided.

Locally, the sample container has to communicate optically with the radiation source and the radiation detector, both of which preferably are located outside the sample container, and it therefore has to be made of a material which is transparent for the relevant radiation at least in the areas communicating with the radiation source and the radiation detector. The material also has to provide the sample container with a sufficient diffusion tightness for oxygen and carbon dioxide, which means that the content of oxygen and/or carbon dioxide may not change substantially during the time normally passing from the sampling to the moment of the analysis. A polymeric base material, if necessary with a coating of a polymeric or metallic gas barrier sheet is supposed to be suitable and the base material is preferably an injection mouldable material. A suitable base material is polyethylene terephtalate (Arnite™ from AKZO, Arnhem, Holland).

As to the handling of samples for clinical chemical analysis an equipment with a cavity sufficiently small for a given sample to be sucked into the cavity by capillary effect is known from the specification of International patent application WO 86/00138 (Shanks el. al.).

In this equipment the cavity is provided with an electrode structure and possibly a coating of a material adapted to the analysis to be performed with the equipment. The electrode structure provided in the cavity may be a potentiometric ion sensitive electrode structure or an amperometric electrode structure. The latter is described in connection with determination of hydrogen peroxide and oxygen in the sample. Supplementary use of the equipment for optical analysis of the products of a specific binding reaction is also described.

From the specification of Danish patent publication no. 150804 (Lilja, J. E. and Nilsson, S. E. L.) is known a sample container for sampling, mixing a sample with at least one reagent and directly performing a separate optical analysis of the sample mixed with the reagent. The sample container has a capillary cavity coated with a reagent and the inlet to the sample container works by capillary effect. The sample container is stated to be useful for most different kinds of analysis and to be especially advantageous for determination of hemoglobin.

From the specification of British patent application GB 2 025 065 (Meiattini, F. et. al.) is known a plunger syringe for withdrawal of a blood sample. The blood sample is analysed by means of sensors incorporated in the syringe plunger. It is thereby avoided to transfer the sample to a sample station.

The sensors are adapted for connection with an analyzer via conductors for registering, processing, and outprinting analysis data. The specific sensors described in the specification of the said British patent application GB 2 025 065 are electrochemical sensors for blood gases and blood electrolytes.

Since the method according to the invention is based on photometric principles, the connection of electric conductors to the sensors of the sample container, which is nescessary when the sensors are electrochemical sensors as in the above described sample containers, is avoided. A more simple design of the sample container and of the interface between the sample container and the respective analyzer is thereby possible.

It shall finally be mentioned that the technological basis also comprises other clinical chemistry analyzers consisting of a combination of disposable components, which are only used for one single analysis operation and only get in touch with one single sample, and an analysing section adapted for receiving the sample containing disposable device and containing the additional components necessary for accomplishing a clinical chemical analysis. Special blood gas analyzers are, however, not known among these.

"Photometric determination" denotes in the present context every determination based on measuring changes in electromagnetic radiation, which under controlled conditions is emitted, transmitted, absorbed, or reflected.

"In vivo locality" denotes in the present context a locality being in direct connection with the blood circulation or being a locality in the blood circulation itself. Sampling by arterial puncture, whereby the blood sample is transferred from the artery to the sample container by a thin needle, as well as via an arterial catheter or via capillary puncture are sampling methodologies, in which the blood sample is transferred directly from an in vivo locality to a sample container.

In the case where the blood sample is provided by capillary puncture, the use of a sample container with a dimension sufficiently small for the sample container to be filled by capillary effect is preferred.

In the case where a sample of arterial blood is desired, the use of a sample container with an inlet located in a coupling means, preferably a Luer cone, for coupling the sample container to a needle or a catheter is preferred.

In the case where the sampling of the blood sample is performed by use of a needle coupled to the sample container, it is especially advantageous to provide the sample container with a needle protecting means integral therewith, preferably a jacket movable in the axial direction of the sample container between a first position, wherein the jacket exposes the point of the needle, and a second position, wherein the jacket surrounds the point of the needle.

With this preferred embodiment of the sample container it is possible to obtain sufficient security for the user against being injured by the needle just by displacing the jacket into the second position. The user is thus not in risk of getting in touch either with the needle carrying part itself or with the immediately surrounding area during removal or application of a protecting means.

Alternatively the needle protecting means can be an elongated gully-shaped element pivotally mounted around an axis located near the inlet of the sample container. During sampling the needle protecting means surround the sample container, while the needle is exposed.

By rotation 180° C. around the axis the needle protecting means are brought to surround the needle, while the sample container is exposed.

The invention also relates to a system for photometric in vitro determination of a blood gas parameter in a blood sample, the system comprising an at least partially transparent sample container and further comprising an analyzer with a sample container station and with an optical system adapted to the relevant blood gas parameter and comprising a radiation source and a radiation detector interacting therewith, the sample container station being so arranged in relation to the radiation source and the radiation detector that a sample container containing blood sample and placed in the sample container station is in locally optical communication with the radiation source and the radiation detector and with means for registering the radiation detected by the radiation detector.

In a preferred embodiment the analyzer comprises data processing means for processing the registered radiation data for deriving the relevant blood gas parameter from these. Alternatively the analyzer is adapted for connection to a separate data processing unit.

In a further preferred embodiment of the system according to the invention the analyzer comprises means for displaying the relevant blood gas parameter or any possible parameters derived from this. Alternatively, the analyzer is adapted for connection with means such as, e.g. a data screen, a display, a printer, or a plotter.

The invention will now be explained in the following with reference to the drawings and the subsequent examples. In the drawings The analysis system shown in FIG. 1 and generally designated 10 is a compact portable "stand-alone" system, which is suited for decentralized use, i.e. use outside a regular laboratory environment, e.g. in an operating room or at an intensive ward. The analysis system 10 comprises a blood sample container 2 for disposable use and used in connection with an analyzer 11. The sample container 2 is more explicitly described in connection with the description of FIGS. 3–5 below. The sample container 2 and the analyzer 11 are adapted to interact in the way that the analyzer 11 has a sample container station 1 with an optical section 3 adapted for receiving the sample container 2, so that the optical communication between the sample container 2 and the optical components of the optical unit 3, which is necessary for photometric analysis, is obtained.

The sample container station 1 can be closed by a cover 8, which is closed after placing the sample container 2 in the station. By closing the cover 8 different mechanisms are activated, e.g. a not shown clamping mechanism, which secures the sample container 2 in the optical section 3 and at the same time thermostatically controls the sample container to a desired temperature, preferably app. 37° C.

Closing the cover 8 further results in a signal being sent to the controlling unit of the analyzer and indicating the start of an analysis procedure. An operator can control the operation of the analyzer by means of a keyboard 5 and a display 6. The analyzer 11 preferably also comprises a printer, which can produce an outprint 7 of the analysis results obtained by the analyzer.

After placing the sample container 2 in the sample container station 1 and closing the cover 8 of this, the optical components comprising of radiation sources and radiation detectors are activated, whereupon the analyzer 11 calculates one or several blood gas parameters on the basis of the signals from the radiation detectors. The result of the calculations is displayed on the display 6 and is printed on the paper outprint 7 by the printer. When the calculations are terminated and the results displayed and/or printed out the cover 8 is opened and the sample container 2 is displaced from the sample container station 1 and removed.

Figure 2:
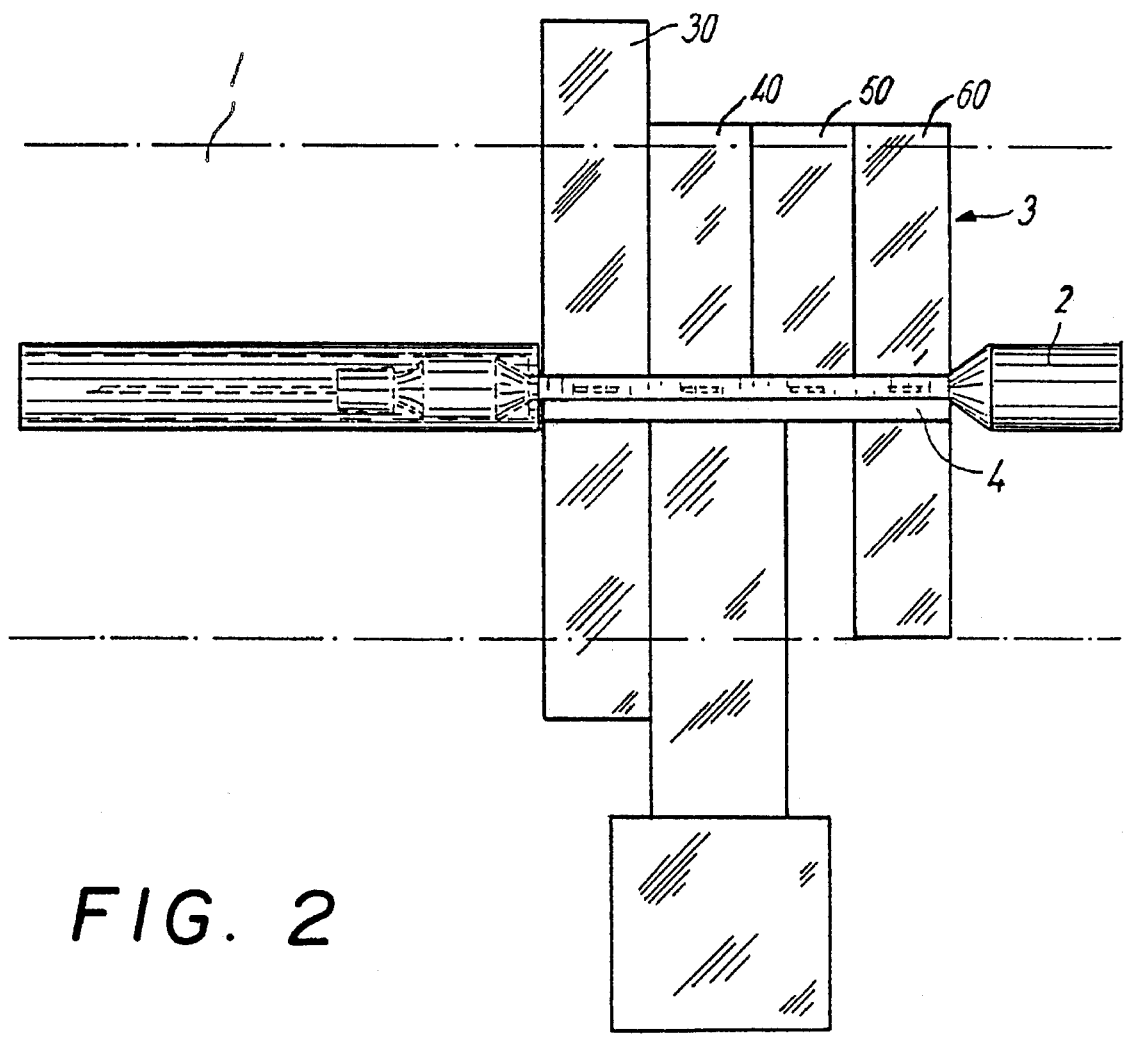
FIG. 2 is an enlarged schematic view from the above sample container station of the analyzer with the sample container.

In a larger scale FIG. 2 shows a partially schematic section of the sample container station 1 viewed from above. As shown the optical section 3 comprises four optical units 30, 40, 50, and 60 each adapted for determination of its relevant blood parameter. The sample container 2 is placed in a slot 4 in the optical section 3.

The optical unit 30 contains the optical components necessary for photometric determination of pH. The optical unit 40 contains the optical components necessary for photometric determination of $CO_2$. The optical unit 50 contains the optical components necessary for photometric determination of $O_2$ and finally the optical unit 60 contains the optical components necessary for photometric determination of hemoglobin. Even though the analyzer 11 is shown containing four optical units it can in principle contain an arbitrary number and/or an arbitrary combination of units, including units adapted for determination of other parameters than those mentioned here.

Figure 3:
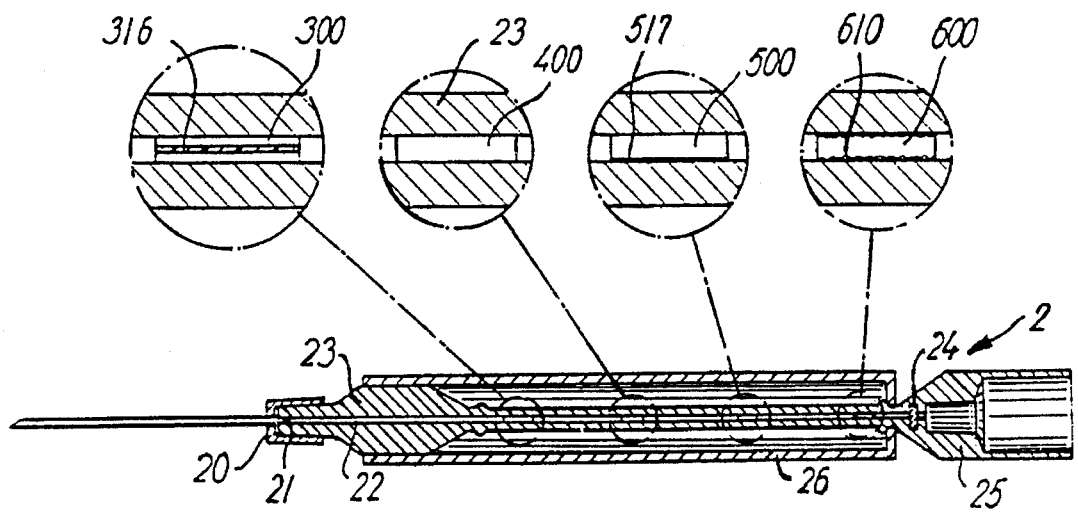
FIG. 3, FIG. 4 and FIG. 5 are views of a preferred embodiment of a sample container for the system according to the invention.

FIG. 3 shows a longitudinal section of the sample container 2 and four segments of this in a larger scale. The sample container comprises a body 23, which at least in specified areas is made of a material transparent for the relevant radiation. The body 23 has a continuous conduit 22 locally extended for forming measuring chambers 300, 400, 500, and 600. During a course of measurement the actual blood sample fills the conduit 22 from its inlet aperture 21 to a hydrophobic filter 24 placed behind the measuring chambers. The section of the body 23 surrounding the inlet aperture is provided with a Luer cone and is therefore suitable for being mounted with a needle 20 of the type normally used for blood sampling. The section 25 of the body 23 pointing away from the inlet aperture is adapted for coupling with a traditional plunger syringe. Such a plunger syringe is used as an aid at the sampling in certain situations, e.g. when the patient, whose blood gas parameters are to be determined, has a very low blood pressure.

When the sample container 2 is placed correctly in the sample container station 1, the measuring chambers 300, 400, 500, and 600 communicate optically with the optical units 30, 40, 50, and 60. The measuring chamber 300 optically communicating with the optical unit 30 is adapted for determination of pH in the blood sample and contains a cellophane membrane 316, to which is immobilized a pH absorbance indicator. When the indicator is in chemical equilibrium with the blood sample, the relation between the acid form of the indicator and the basic form of the indicator reflects the pH-value of the blood sample. The chemical and photometric basis for the pH determination appears from FIGS. 7, 11, and 15 and of the description of these. An embodiment of the optical unit 30 appears from FIG. 15 and the description of this.

The measuring chamber 400 communicates optically with is the optical unit 40 adapted for determination of the carbon dioxide content in the blood sample. As it is seen from FIGS. 8, 12, and 16 and the description of these, this determination takes place on the basis of the transmission properties of the sample for radiation at the wavelength 4260 nm. An embodiment of the optical unit 40 appears from FIG. 16 and the description of this.

The measuring chamber 500 is the measuring chamber wherein the determination of the oxygen content of the sample takes place and this measuring chamber communicates optically with the optical unit 50. On one of its surfaces the measuring chamber 500 has a PVC membrane 517 dyed with the phosphorescent compound PdTFPP (palladium (II)-tetra(pentafluorphenyl)-porphyrin). The phosphorescent compound is excited with radiation of a wavelength at app. 556 nm, and the oxygen content is determined by determining characteristics of radiation at the wavelength 673 nm emitted from the excited phosphorescent compound. The chemical and photometric basis for the oxygen determination appears from FIGS. 9, 13, and 17 and the description of these. An embodiment of the optical unit 50 appears from FIG. 17 and the description of this.

The measuring chamber 600 is the measuring chamber wherein the hemoglobin content and the oxygen saturation of the blood sample is determined. The measuring chamber is adapted to optically communicate with the optical unit 60 and has a coating 610 of a chemical hemolysis agent on its internal surface. The hemoglobin content in the blood sample is determined by determining characteristics of radiation at the wavelengths 506 nm and 600 nm transmitted through the blood sample. The chemical and photometric basis for the determination of hemoglobin appears from FIGS. 10 and 18 and from the description of these. An embodiment of the optical unit 60 appears from FIG. 18 and the description of this.

The exterior walls of the measuring chambers 300, 400, and/or 500 are preferably made by a material different from the base material of the sample container 2. An ethylene vinylalcohol copolymer of the type EVAL-E™ from Kuraray Co., Osaka, Japan is suited for application as measuring chamber walls due to its low oxygen and carbon dioxide permeability and its adequate optical properties. Another suitable material for wall elements constituting the exterior walls of the measuring chambers 300, 400, and/or 500 is glass.

Finally it appears from FIG. 3 that the sample container 2 has an integral needle protecting means 26. In the embodiment shown the needle protecting means 26 is a tubular jacket movable in the axial direction of the sample container between a first position, wherein the jacket exposes the point of the needle, and a second position, wherein the jacket surrounds the point of the needle.

FIG. 3 shows the protecting jacket 26 in the first position, in which it is placed at the sampling moment.

Figure 4:
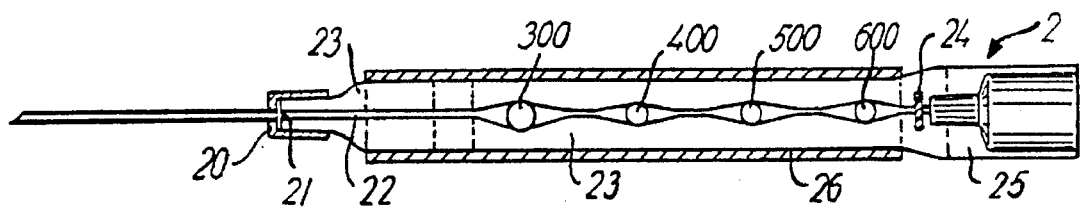

FIG. 4 shows a longitudinal section of the sample container. The section is placed perpendicular to the section shown in FIG. 3.

The sample container body 23 consists of two halves, of which only one is visible in FIG. 4.

Figure 5:
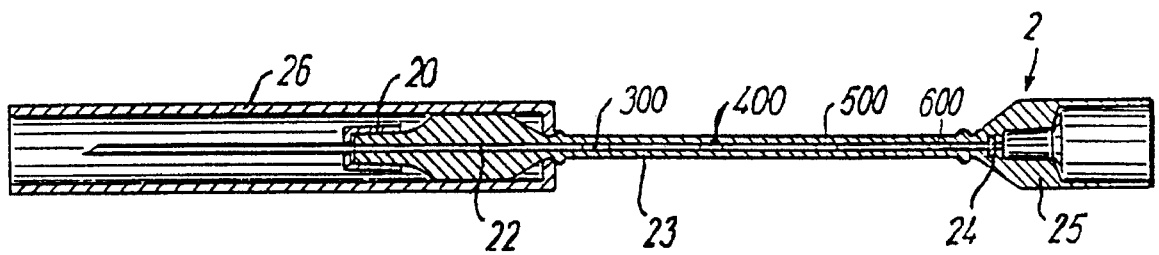

FIG. 5 shows finally the same section as FIG. 3 but in FIG. 5 the protecting jacket is displaced to the second position, wherein it surrounds the point of the needle. The jacket 26 is displaced to this second position immediately after the sampling.

Figure 6:
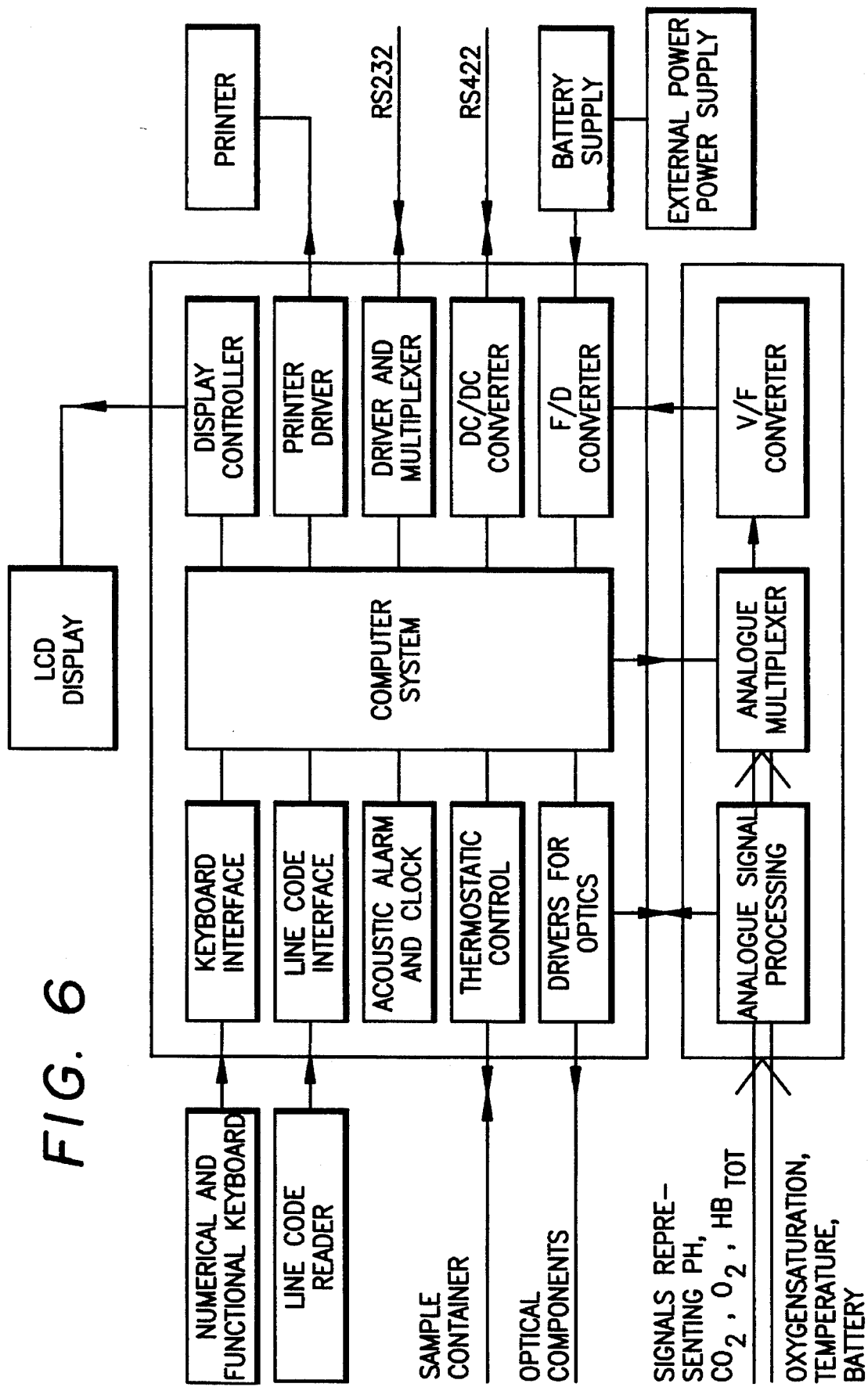
FIG. 6 is an electric block diagram of the analyzer shown in FIG. 1.

FIG. 6 shows the electrical block diagram for the analyzer 11 and speaks for itself.

Figure 7:
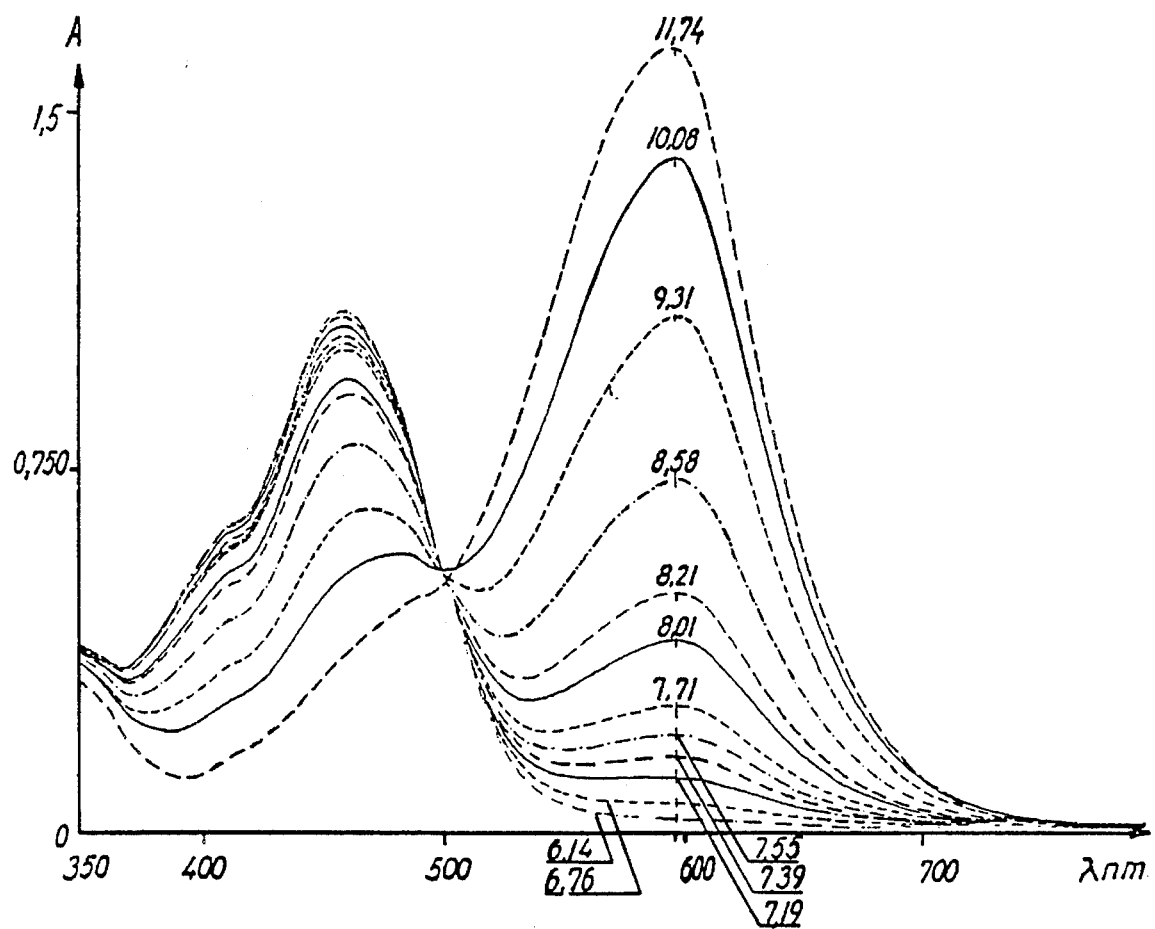
FIG. 7 shows the photometric basis for determination of the blood gas parameter pH.

FIG. 7 shows the absorption spectrum for a pH absorption indicator N-9 more closely described below in connection with FIG. 11. The indicator is immobilized on a cellophane membrane by the method also described in detail in connection with FIG. 11. The spectrum is recorded by a spectrophotometer of the type Shimadzu Spectrophotometer UV 250. The absorption measurements were performed on a cellophane membrane (6×12×0.028 mm) with immobilized indicator. The cellophane was placed in the cuvette of the spectrophotometer in a holder adapted thereto and with dimensions adapted to the dimensions of the cuvette.

In order to determine the absorption conditions at different pH-values, a number of pH buffers with pH values in the pH range from pH 6.14–11.74 was produced. Each buffer consisted of 500 ml 0.1M $KH_2PO_4$ to which was added the necessary amount of 0.1M NaOH. The pH value of each buffer was potentiometrically measured (Radiometer PHM80) by means of a glass electrode (Radiometer GK2402C).

It appears from the spectrum shown in FIG. 7 that the acid form of the indicator has an absorption top at 458 nm and that the basic form of the indicator has an absorption top at 595 nm and that the indicator not essentially absorbs radiation at wavelengths above 750 nm.

Figure 8:
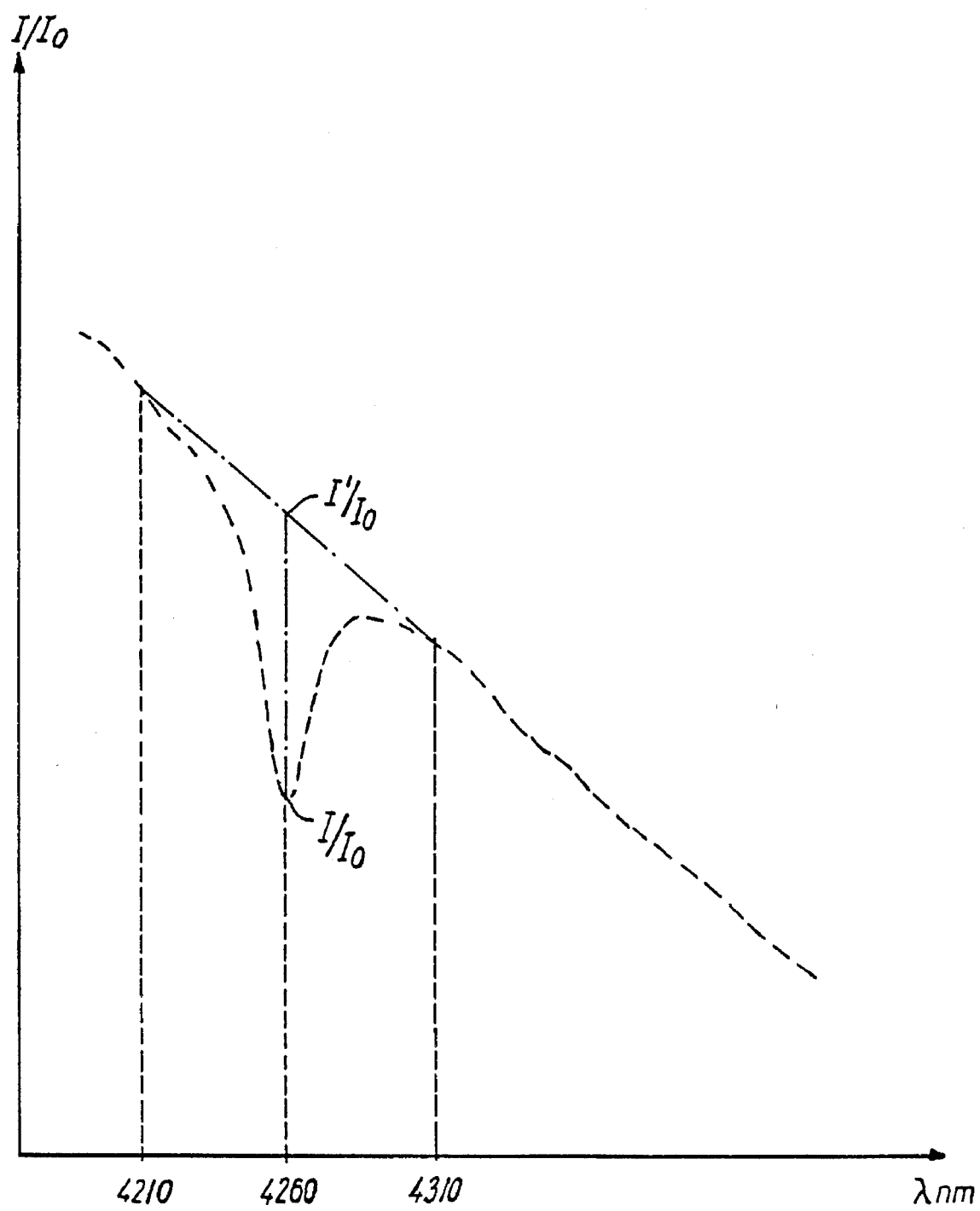
FIG. 8 shows the photometric basis for determinatioin of the blood gas parameter $CO_2$.

FIG. 8 shows an absorption spectrum for whole blood (hemoglobin content 9 mmol/l, $Pco_2$ 419 mmHg) recorded on an IR spectrophotometer of the type Beckman IR9. From the absorption spectrum it appears that a content of $CO_2$ in the blood sample results in an absorption at about 4260 nm.

Figure 9:
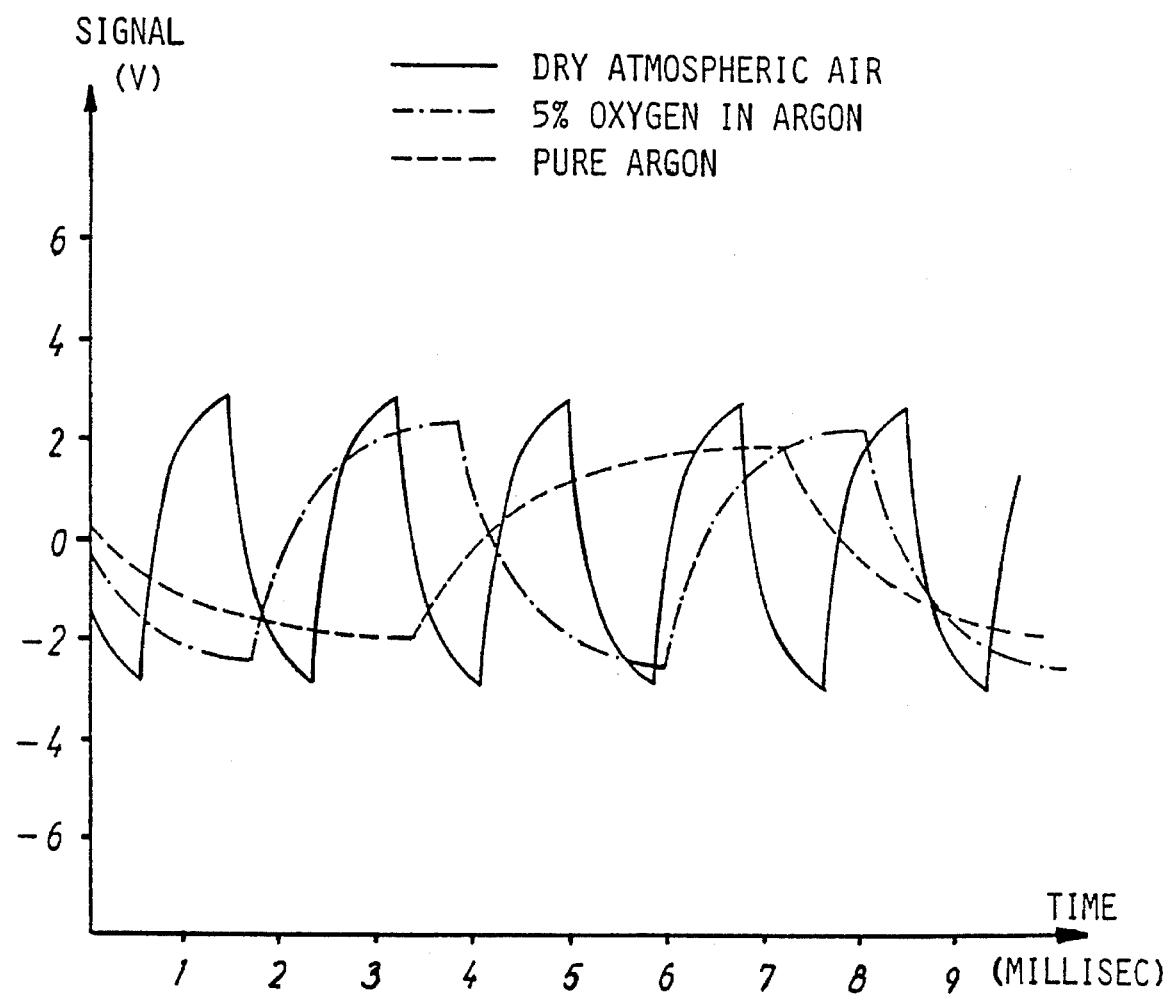
FIG. 9 shows the photometric basis for determination of the blood gas parameter $O_2$.
Figure 19:
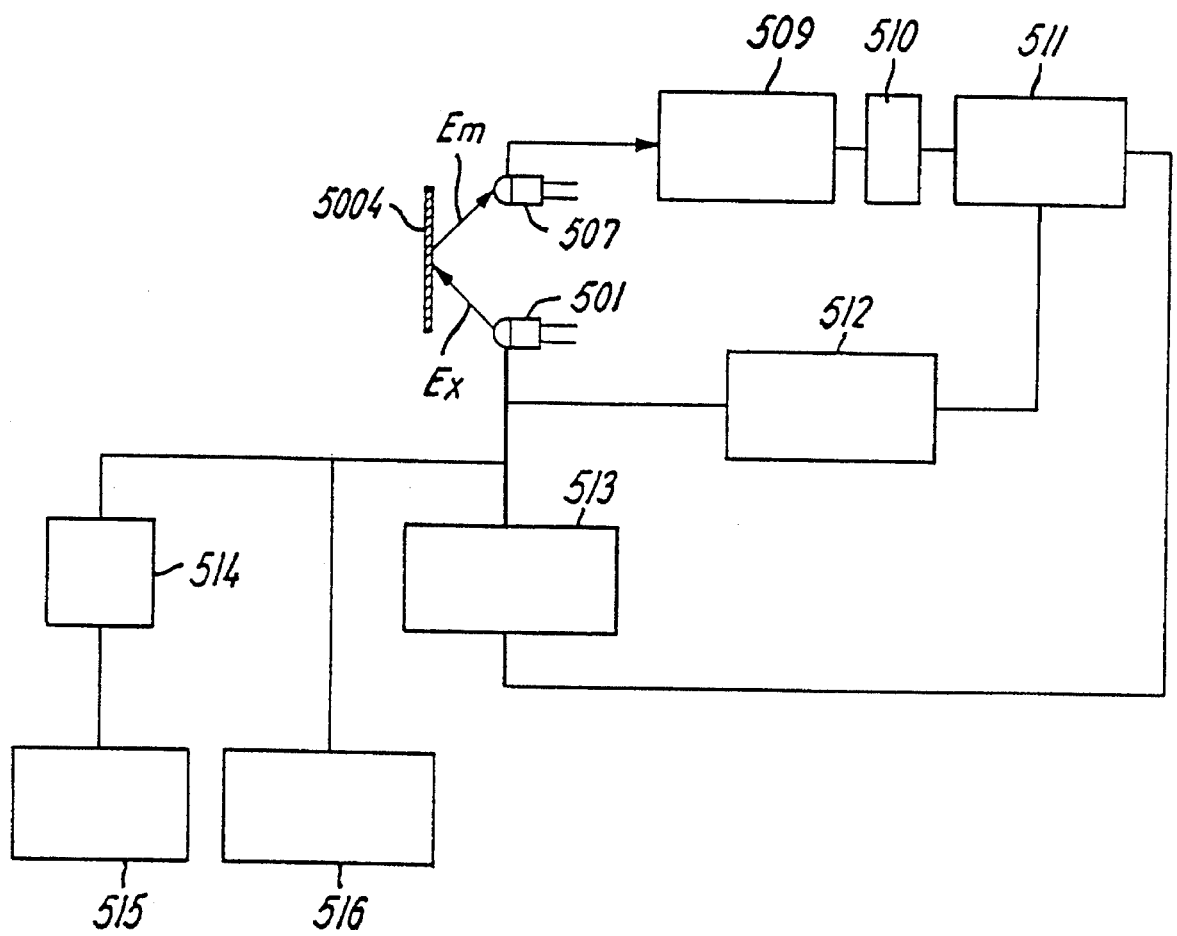
FIG. 19 is a block diagram of the electronic circuit coupled to the optical unit for photometric determination of $O_2$.

For each of three different oxygen levels in gaseous samples FIG. 9 shows a signal representing the time dependent emission radiation from a luminophor excited with a modulated excitation source. It appears from the figure that the frequency of the signal depends on the oxygen content. The figure is provided by use of the sample container according to FIG. 13 and the optical unit according to FIG. 17 with electronics as shown in FIG. 19 and an oscilloscope coupled thereto.

Figure 10:
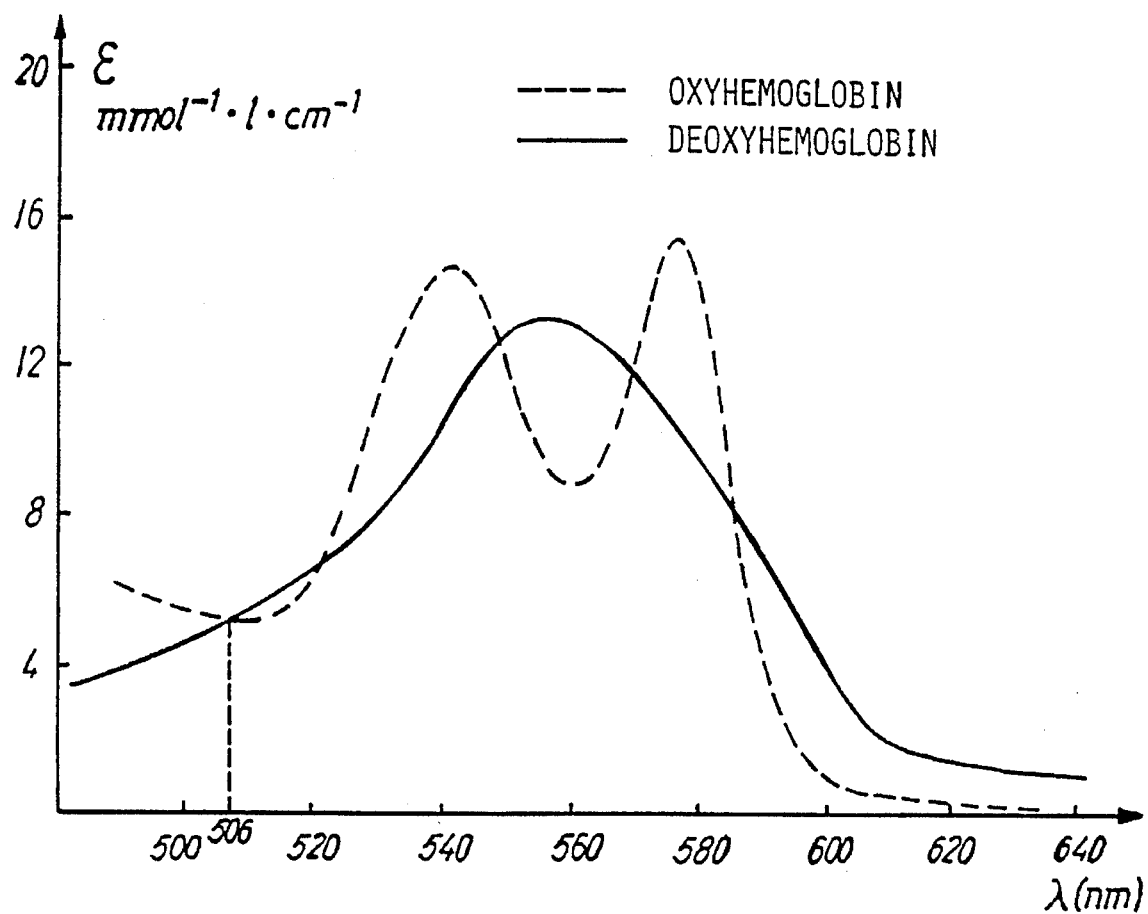
FIG. 10 shows the photometric basis for determination of the hemoglobin content.

FIG. 10 shows the absorption spectra for oxyhemoglobin and deoxyhemoglobin, respectively. The two absorption spectra intersect in an isobestic point situated at the wavelength 506 nm. The total hemoglobin content of a blood sample can be determined on the basis of the transmission properties of the sample for radiation at the wavelength 506 nm, as $Hb_{tot}$ is the sum of the content of oxyhemoglobin and the content of deoxyhemoglobin. On the basis of the transmission properties of the sample for radiation at another wavelength the content of, e.g., oxyhemoglobin can be determined and thereby also the oxygen saturation (oxyhemoglobin/$Hb_{tot}$). The absorption spectrum shown here is reproduced from Zijlstra, W. G. et al. "Problems in the spectrophotometric determination of $HbO_2$ and HbCO in fetal blood", Physiology and Methodology of Blood Gas and pH, volume 4, 1984, 45–55.

FIG. 11 shows an embodiment of a sample container for use in determination of pH in a blood sample. The sample container generally designated 3000, is intended to interact with an analyzer with an optical unit as the one more closely described below in connection with FIG. 15. The sample container consists of two halves 3001 and 3002. These halves are made from a transparent plastic material, e.g., softened polymethyl methacrylate of the type DEGALAN™ SZ70 (Superfos, Copenhagen, Denmark). The two halves are assembled by pins 3005 and 3006 in the half 3001 engaging corresponding, not shown recesses in the half 3002, while not shown pins in this engage recesses 3007 and 3008 in the half 3001. The two halves are hereafter welded together by ultrasonic welding. The line 3009 of material outlined on the lower half 3001 shown in the figure forms a welding seam after the welding. This line of material lies along the edge of a longitudinal conduit 3004, which centrally expands transversely and forms a measuring chamber 3011. A wall section 3010 of the upper half 3002 shown in the figure has to be elastically deformable and for that reason has a very reduced wall thickness compared to the rest of the half. As mentioned in connection with FIG. 7 a cellophane membrane 3003, to which there is immobilized a pH indicator, is placed in the measuring chamber 3011.

Preparation of the Cellophane Membrane with Immobilized pH Indicator

The pH indicator is delivered by Merck, Darmstadt, West Germany under the name N-9 and is known to contain the reactive group

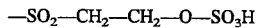
$$-SO_2-CH_2-CH_2-O-SO_3H$$

The immobilization of the indicator to the membrane takes place in a process, whereby the above mentioned reactive group is transformed with sodium hydroxide into a vinyl sulphone group, which can be coupled to cellophane previously activated by conditioning the cellophane in 0.1M NaOH for 15 minutes.

The reaction scheme describing the coupling reaction between the indicator and the cellophane membrane is:

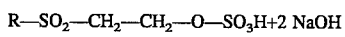
$$R-SO_2-CH_2-CH_2-O-SO_3H+2\,NaOH$$

$$R-SO_2-CH=CH_2+Na_2SO_4+2\,H_2O \qquad (1)$$

$$R-SO_2-CH=CH_2+HO\text{-cellophane}$$

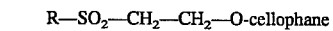
$$R-SO_2-CH_2-CH_2-O\text{-cellophane} \qquad (2)$$

R here designates an aryl group.

The quantitative immobilization procedure is the following: 100 mg cellophane (of the type 113650–36/32 from Struers, Copenhagen, Denmark) is after the above mentioned conditioning with NaOH prepared with an indicator solution consisting of 6 mg N-9, 1000 mg NaCl, 500 mg $Na_2CO_3$, 200 µl 8M NaOH in 40 ml $H_2O$. The cellophane is left in the indicator solution for 30 minutes. Hereafter the cellophane is removed from the indicator solution and washed several times with deionized water, whereafter it is left in deionized water at least through the night before use.

The prepared membrane is then kept in deionized water until use.

FIG. 12 shows an embodiment of a sample container for use in determination of the content of carbon dioxide in a blood sample. The sample container, generally designated 4000, is intended to interact with an analyzer with an optical unit as the one described below in connection with FIG. 16. The sample container 4000 consists of two halves designated 4001 and 4002, respectively. The two halves are assembled in the same way as the sample container 3000 according to FIG. 11. After the assembly, the sample container has analogously hereto an internal sample conduit 4006, which centrally expands transversely for forming a measuring chamber 4007. The two halves 4001 and 4002 are made from a plastic material, but the measuring chamber itself is in a direction perpendicular to the conduit 4006 defined by two glass plates or alternatively EVAL-E™ plates 4003 and 4004 secured between the two halves. One or several very thin lines 4005 of material ensure a well defined distance, e.g. 35 μm, between the two plates 4003 and 4004.

FIG. 13 shows a sample container for use in determination of the oxygen content in a blood sample. The sample container, generally designated 5000, is intended to interact with an analyzer with an optical unit as the one described below in connection with FIG. 17. The sample container 5000 consists of two halves designated 5001 and 5002, respectively. The two halves are assembled in the same way as the sample container 3000 according to FIG. 11. Thus, after the assembly the sample container has a sample conduit 5006, which centrally expands transversely into a measuring chamber 5007. The two halves 5001 and 5002 are made from a plastic material. One of the walls in the measuring chamber 5007 consists of a glass plate 5003 in the form of a microscope cover glass, or alternatively an EVAL-E™ plate, on which there is cast a 2 μm coating 5004 of PVC containing PdTFPP. The preparation of the element consisting of the plate 5003 and the PVC coating 5004 is more closely described below. A double adhesive ring 5005 secures the plate 5003 to the sample container part 5002.

Preparation of the Wall Element with Luminophor

A solution consisting of 15 mg PdTFPP (synthesized for the applicant for the purpose), 199.5 mg PVC (BREON S 110/10; BP Kemi, Copenhagen, Denmark) and 1.5 ml tetrahydrofuran (LiChrosolv™; Merck, Darmstadt, West Germany) is cast on a rotating microscope cover glass etched by hydrofluoric acid in a dry atmosphere by putting on 10 μl solution as drops. The speed of rotation is 110–120 rotations/ sec.

Less than two hours after the casting the wall element is placed at 90° C. in an incubator for 40 minutes, whereby the PdTFPP containing PVC coating is hardened.

The membrane thickness is reproducible and is about 2 μm.

FIG. 14 shows a holder 7000 for the sample container 4000. The holder has a recess 7001 adapted to the sample container 4000 and intended for receiving this. The holder 7000 is intended to be placed in an optical unit, e.g. the optical unit 40 according to FIG. 16 described below or the optical unit 60 according to FIG. 18 described below. When the holder 7000 is placed in one of the optical units mentioned, a hole 7002 secures the optical communication between the sample container and the radiation source. The holder 7000 is preferably made from a well heat conducting material, e.g. aluminium.

Figure 15:
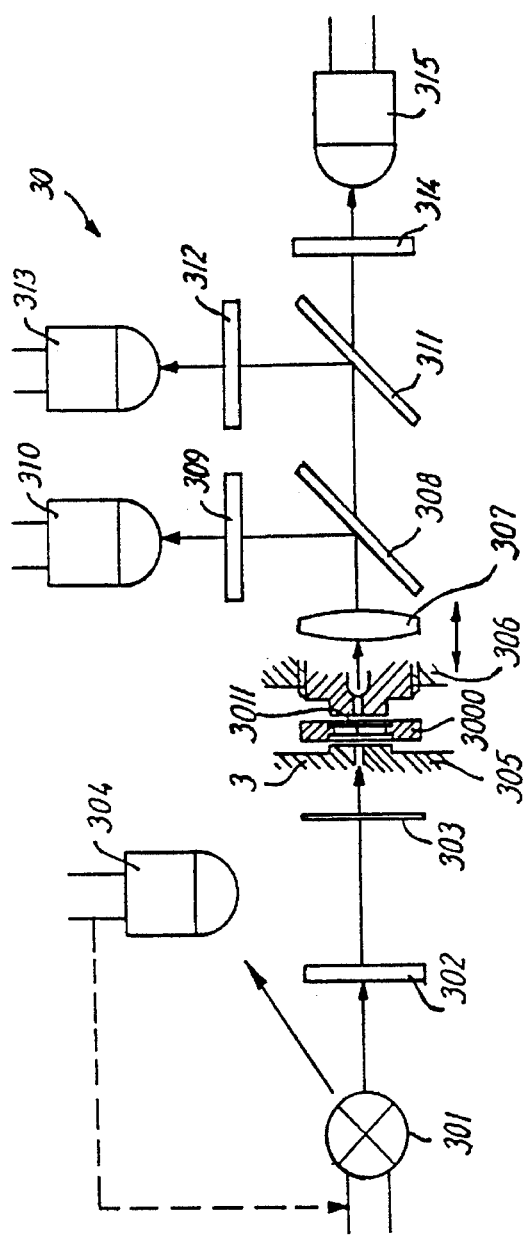
FIG. 15 is a partial cross section of an optical unit in a system according to the invention for photometric determination of pH and with a schematic representation of the components forming parts of the optical unit.

FIG. 15 shows a prototype of an optical unit 30 for use in determination of pH in a blood sample. The blood sample is located in the measuring chamber 3011 in the sample container 3000, which is secured between a stationary part 305 and a moving part 306. The previously mentioned membrane with immobilized pH-indicator is provided in the measuring chamber. Before the measuring, the blood is pressed away from the measuring chamber by pressing the moving part 306 against the adjacent wall of the measuring chamber 3011. Pressing out the blood sample from the measuring chamber results in the transmission conditions inside the measuring chamber not being influenced by the blood sample itself.

The optical unit 30 works in following way: A radiation source 301 in the form of a halogen lamp with a builtin lens of the type LNS-SE6-560 from Hamai Electric Lamp Co. TTD, Tokyo, Japan emits a parallel beam of broadbanded radiation. This radiation is transmitted to a heat absorbing filter 302 of the type KG 5 from Schott, Mainz, West Germany. This filter eliminates radiation from the infrared range. The radiation is transmitted from the filter to a depolarizer 303 and from there through the measuring chamber 3011. A silicon photodiode 304 of the type SFH 212 from Siemens, Munich, West Germany, receives radiation reflected from different surfaces inside the optical unit and is coupled to the radiation source 301 and ensures constant radiation intensity from this.

After passage through the measuring chamber 3011, the radiation is focused by a lens 307 (φ12 mm; f 12 mm; Thermooptik Arnold GmbH & Co., Weilburg, West Germany) onto three silicon photodiodes 310, 313 and 315, which are all of the type SFH 212 and situated in the focal plane of the lens 307. From the lens 307 the radiation is transmitted to a dichroic mirror 308 reflecting radiation of wavelengths less than 560 mm and transmitting radiation of longer wavelengths. The dichroic mirror is delivered by Optisk Laboratorium, Technical University of Denmark, Lyngby, Denmark. The short-waved part of the radiation passes through a band-pass filter 309 (centre value 458 nm; half band width 5.1 nm; Ferroperm, Vedbaek, Denmark) and is transmitted from the band-pass filter 309 to a silicon photodiode 310 of the type SFH 212. The part of the radiation from the lens 307 transmitted through the dichroic mirror 308 is transmitted to another dichroic mirror 311 reflecting radiation of wavelengths less than 690 nm and transmitting the more long-waved radiation. The dichroic mirror is again delivered by Optisk Laboratorium, Technical University of Denmark, Lyngby, Denmark. The reflected radiation is transmitted from the dichroic mirror 311 through a bandpass filter 312 (centre value 589 nm, half band width 14.8 nm; Ferroperm, Vedbaek, Denmark) and from there to a silicon photodiode 313 of the type SFH 212. The radiation transmitted through the dichroic mirror 311 is transmitted from here to a bandpass filter 314 (centre value 750 nm; half band width 10 nm; Ferroperm, Vedbaek, Denmark) and from there to a silicon photodiode 315 of the type SFH 212. The silicon photodiodes 310, 313 and 315 emit a current signal representing the intensity of 458 nm, 589 nm and 760 nm radiation, respectively. On the basis of these radiation intensities the pH value of the sample is calculated.

More precisely the pH value of the sample is calculated in the following way:

With different samples in the form of blood sample as well as the below mentioned two pH buffers in the sample container is for each wavelength $\lambda_1, \lambda_2, \lambda_3$ determined the current $I_{background,\lambda}$ measured on the corresponding photodiode for a sample container containing a cellophane membrane without immobilized indicator (i.e. a clear cellophane membrane) and sample. This current corresponds to $I_0$ (cf. Lambert Beer's Law). From the knowledge of the dynamic area of the amplifier for the individual photodiode the current $I_{background,\lambda}$ can be related to the absorbance $A_{background,\lambda}$, as $$A_{background,\lambda} = k \cdot \log I_{background,\lambda}$$

where k is a constant.

In the measuring situation where the sample container contains a cellophane membrane prepared with pH indicator, the current $I_{measurement,\lambda}$ also relating to $A_{measurement,\lambda}$ is determined, whereupon the "true" absorbance at the wavelength $\lambda$ is determined as $$A_\lambda = A_{measurement,\lambda} - A_{background,\lambda},$$

cf. $A = \log I - \log I_0$.

To correct further for drift in the optical system, unclear sample containers or other variations not directly relating to the pH determination, the absorbances $A_{\lambda 1}$ and $A_{\lambda 2}$ are corrected with $A_{\lambda 3}$, and the "new" absorbance values are designated $A'_{\lambda 1}$ and $A'_{\lambda 2}$.

The relation to Lambert Beer's Law hereafter appears as:

$$A'_{\lambda 1} = A_{\lambda 1} - A_{\lambda 3} = \epsilon_{\lambda 1, HIn} \cdot c_{HIn} \cdot 1 + \epsilon_{\lambda 1, In^-} \cdot c_{In^-} \cdot 1$$

$$A'_{\lambda 2} = A_{\lambda 2} - A_{\lambda 3} = \epsilon_{\lambda 2, HIn} \cdot c_{HIn} \cdot 1 + \epsilon_{\lambda 2, In^-} \cdot c_{In^-} \cdot 1 \quad (3)$$

where HIn designates the acid form of the pH indicator, In$^-$ designates the basic form of the indicator, $c_{HIn}$ and $c_{In^-}$ in the concentration of the acid and the basic form, respectively, of the indicator, $\epsilon$ the extinction coefficient for the wavelength and compound defined by the suffix, and 1 the pathlength of the radiation through the sample, which can be inverted to:

$$c_{HIn} = k_{11} A'_{\lambda 1} + k_{12} A'_{\lambda 2}$$

$$c_{In^-} = k_{21} A'_{\lambda 1} + k_{22} A'_{\lambda 2} \quad (4)$$

The constants $k_{11}$, $k_{12}$, $k_{21}$, and $k_{22}$ are determined by measuring $A_{\lambda 1}$, $A_{\lambda 2}$ and $A_{\lambda 3}$ with two pH buffers with known pH values as samples. For each of these pH buffers the proportion $c_{In^-}/c_{HIn}$ is determined according to the Henderson Hasselbalch equation:

$$pH = pk_a + \log [c_{In^-}/c_{HIn}] \quad (5)$$

If it is further supposed that $c_{In^-} + c_{HIn} = 1$, the two sets of connected values of $c_{In^-}$ and $c_{HIn}$ can be calculated. If the corrected absorbance values are inserted in the equation set (4), four equations with the four unknown quantities $k_{11}$, $k_{12}$, $k_{21}$, and $k_{22}$ are obtained, and subsequently these four quantities can be calculated.

By measuring unknown samples it is hereafter possible to determine $c_{HIn}$ and $c_{In^-}$ from the equation set (4) and subsequently pH from equation (5).

Figure 16:
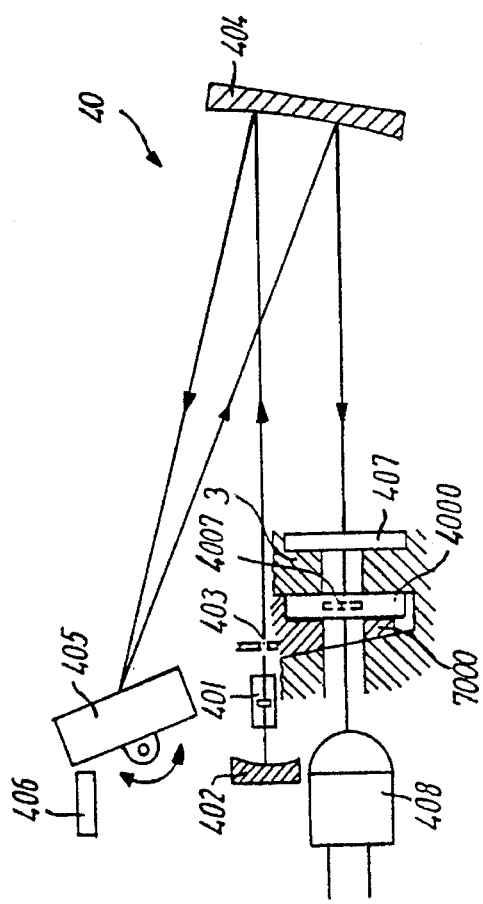
FIG. 16 is a partial cross section of an optical unit in a system according to the invention for photometric determination of $CO_2$ and with a schematic representation of the components forming parts of the optical unit.

FIG. 16 shows a prototype of an optical unit 40 for use in determination of carbon dioxide in a blood sample. The blood sample is located in the measuring chamber 4007 in the sample container 4000 placed in a holder 7000, which further is placed in a unit, generally designated 3. The optical unit 40 contains a radiation source 401 in the form of a thermic radiation unit, more definitely a CrNi filament heated to app. 1000° C. The radiation source is produced for the purpose by the applicant. Radiation from the radiation source 401 is transmitted to a concave mirror 402 of the type 4001021 (φ10 mm; f 5 mm; Thermooptik Arnold GmbH & Co., Weilburg, West Germany).

The concave mirror 402 depicts the filament 401 into a slit 403, and the radiation is transmitted from here to a concave mirror 404. The mutual orientation of the slit 403 and the concave mirror 404 is, that the slit 403 is situated in the focal point of the concave mirror. From the concave mirror 404 produced by the applicant for the present purpose radiation is transmitted to a grating 405 of the type OEM 300-40000-2525 from Optometrics, Leeds, England. The grating is a 300 lines grating optimized to app. 4 µm.

The grating 405 is pivotally mounted and is continuously rotated between two end positions. An optical position detector 406 reads the position of the grating 405. The position of the grating 405 determines the wavelength of the radiation, which at a certain moment passes through the sample container. The actual wavelength is in the range from 4220 to 4310 nm. From the grating 405 the radiation is transmitted back to the concave mirror 404 from where the radiation is reflected, and the radiation relevant to the measurement, i.e., the radiation subsequently passing the sample container, is transmitted through a LWP filter 407 (long wave pass filter) of the type LP 3500-F from Spektrogon, Täby, Sweden. This filter transmits radiation at wavelengths greater than 3500 nm. From the filter 407 the radiation is transmitted through the measuring chamber 4007 and from there to a pyroelectrical detector 408 of the type KRX11 from Philips, Eindhoven, Holland.

The pyroelectrical detector emits a voltage signal proportional to the intensity of the radiation incident on the detector. Detector signals representing the intensity of 4210 nm radiation, 4260 nm radiation, and 4310 nm radiation are registered, so that by means of the position detector 406 it is ascertained when the grating is situated in the first end position (corresponding to transmitting 4210 nm radiation through the sample), the center position (corresponding to transmitting 4260 nm radiation through the sample) and the second end position (corresponding to transmitting 4310 nm radiation through the sample), respectively, and registration of the detector signals shall take place at these moments.

The optical unit 40 described here is intended for determination of $CO_2$ by the so-called baseline analysis method. By this method is calculationwise found an absorbance of a sample not containing $CO_2$ at the wavelength, at which the $CO_2$ absorption top is situated. The baseline analysis method is comprehended by viewing FIG. 8. From the curve for whole blood with $Pco_2$ 419 mm Hg and from the construction line marked with points it is seen that the transmittance $I'/I_0$ of a sample free of $CO_2$ can be estimated by interpolation between the radiation intensities at two wavelengths situated close to and outside the absorption top, in the current case 4210 nm and 4310 nm. Designating the actual transmittance $I/I_0$ the carbon dioxide concentration [$CO_2$] is calculated from Lambert Beer's Law in the following way:

$$\log I_0/I - \log I_0/I' = \epsilon CO_2, 4260 \cdot [CO_2] \cdot 1$$

where $\epsilon CO_2, 4260$ is the extinction coefficient for $CO_2$ at 4260 nm and 1 is the pathlength of the radiation through the sample.

Figure 17:
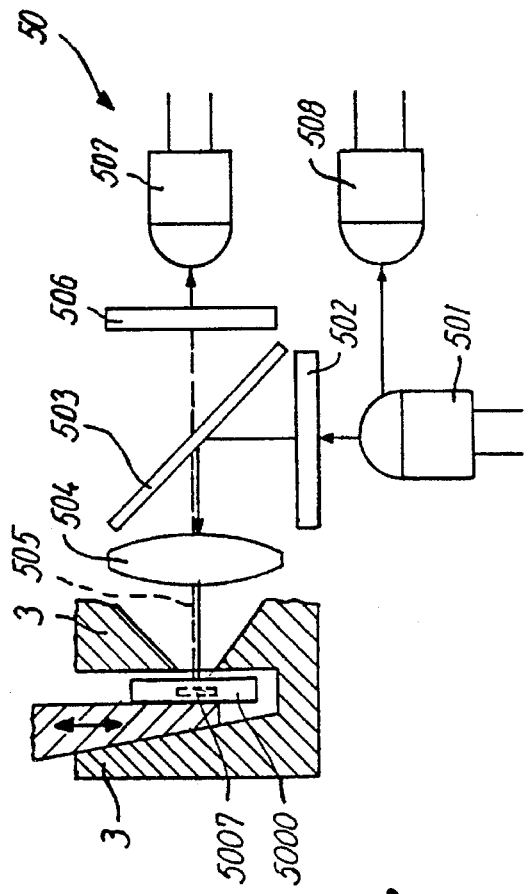
FIG. 17 is a partial cross section of an optical unit in a system according to the invention for photometric determination of $O_2$ and with a schematic representation of the components forming parts of the optical unit.

FIG. 17 shows a prototype of an optical unit 50 for use in determination of oxygen in a blood sample. The blood sample is located in the measuring chamber 5007 in the sample container 5000.

The sample container is placed in a section, generally designated 3.

From a radiation source 501 in the form of a modulated green light diode of the type HBG 5566X from Stanley Electric Co. Ltd, Tokyo, Japan radiation is transmitted through a SWP filter 502 (short wave pass filter), which is specially produced for the applicant for the present purpose, and which eliminates radiation of wavelengths greater than 580 nm. From the filter 502 the radiation is transmitted to a dichroic mirror 503 of the type BSP600 from Optisk Laboratorium, Technical University of Denmark, Lyngby, Denmark. The dichroic mirror 503 reflects radiation at wavelengths less than 600 nm and thereby reflects the radiation from the green light diode. The radiation is reflected from the dichroic mirror to a convex lens 504 ($\phi$9.9 mm; f 7.3 mm; Thermooptik Arnold GmbH & Co., Wellburg, West Germany).

The mutual orientation between the lens 504 and the sample container 5000 is so that the sample container 5000 is situated in the focal plane of the lens. The radiation is focused on the sample container by the lens 504, where it excites a luminophor provided in the measuring chamber 5007. The excited luminophor interacting with the oxygen of the blood sample emits more longwaved radiation 505, which is transmitted from the sample container through the lens 504 and the dichroic mirror 503 to an edge filter 506 of the type RG665 from Schott, Mainz, West Germany. The filter transmits radiation of wavelengths greater than 665 nm. The radiation transmitted through the filter 506 falls onto a silicon photodiode 507 of the type SFH 216 from Siemens, Munich, West Germany, and the photodiode emits a time dependent electrical signal representing the actual radiation intensity. In FIG. 17 is finally shown a silicon photodiode 508 of the same type as the photodiode 507. The purpose of this photodiode is to determine where in its modulation cycle the radiation source is at a certain moment.

By excitation of a luminophor with a sinus modulated excitation radiation applies for a luminophor undergoing monoexponental decay:

$$\omega \cdot \tau = \tan \phi$$

where $\omega$ is the angular frequency of the excitation radiation, $\tau$ is the life time of the emission radiation, and $\phi$ is the phase shift of the emission radiation. If the phase shift between the emission radiation and the excitation radiation is electronically maintained at 45° (tan $\phi$=1) applies:

$$\omega = 1/\tau$$

and thus, according to the wellknown Stern-Volmer equation:

$$\omega/\omega_0 = 1 + K_{sv} \cdot [O_2]$$

where $\omega_0$ is the angular frequency of the excitation radiation at an oxygen concentration of 0, $K_{sv}$ is the so-called Stern-Volmer constant and $[O_2]$ is the oxygen concentration.

For known values of $\omega_0$ and $K_{sv}$ the oxygen content $[O_2]$ can thus be determined on the basis of detecting the angular frequency $\omega$ or the frequency $f=\omega/2\pi$ of the excitation radiation. In practice the decay is not mono-exponential and a linear relation between $\omega$ (or f) and $O_2$ is therefore not seen. A reproducible relation has, however, appeared obtainable not just for sinus modulated excitation radiation, but also for excitation radiation modulated in other ways, i.e. square wave modulated excitation radiation.

A simple electronic circuit whereby $\omega$ or f can be determined is shown in FIG. 19.

Figure 18:
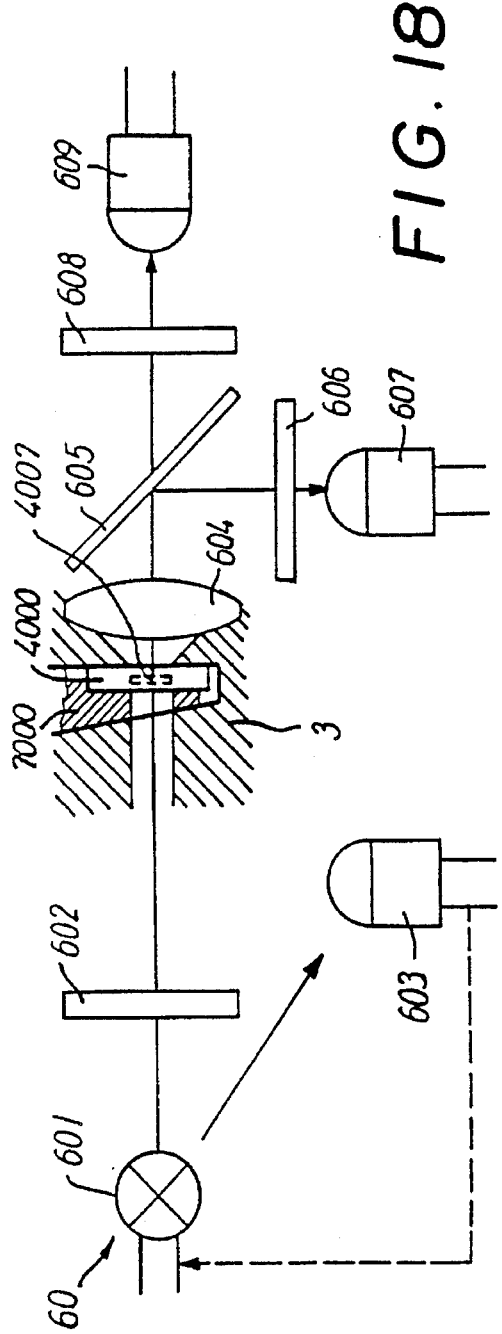
FIG. 18 is a partial cross section of an optical unit in a system according to the invention for photometric determination of hemoglobin and with a schematic representation of the components forming parts of the optical unit.

FIG. 18 shows a prototype for an optical unit 60 for use in determination of the hemoglobin content of a blood sample. The blood sample is located in the measuring chamber 4007 in the sample container 4000.

The sample container 4000 is placed in a holder situated in a section, generally designated 3. Broad-banded radiation is transmitted from a radiation source 601 in the form of a halogen lamp with built-in lens of the type LNS-SE6-560 from Hamai Electric Lamp Co. TTD., Tokyo, Japan, to a heat absorbing filter 602 of the type KG5 from Scott. The filter 602 eliminates radiation from the infrared range. The radiation is transmitted from there to the measuring chamber 4007 and further to a convex lens 604, which focus the radiation onto two radiation detectors 607 and 609. From the convex lens 604 the radiation is transmitted to a dichroic mirror 605 from Optisk Laboratorium, Technical University of Denmark, Lyngby, Denmark, which reflects radiation of wavelengths less than 560 nm and transmits radiation of wavelength greater than 560 nm.

The reflected radiation is transmitted from the dichroic mirror to a band-pass filter 606 (centre value 506 nm; half band width 6 nm; Ferroperm, Vedbaek, Denmark) and from the filter to a radiation detector 607 of the type SFH 212 from Siemens. The radiation passing through the dichroic mirror is transmitted to a band-pass filter 608 (centre value 600 nm; half band width 6 nm; Ferroperm, Vedbaek, Denmark) and to a silicon photodiode 609 of the type SFH 212 corresponding to the silicon photodiode 607. Finally a silicon photodiode 603 of the same type as the photodiodes 607 and 609 receives radiation reflected from different surfaces.

The intensity of the radiation source 601 is regulated on the basis of the radiation received by the silicon photodiode 603, aiming at a constant radiation intensity from the radiation source 601. Calculation of the total hemoglobin content $Hb_{tot}$ and the oxygen saturation can subsequently be fulfilled on the basis of the diode signals. The calculation is performed in a wellknown way according to Lambert Beer's Law from predetermined values of the extinction coefficients for Hb and $HbO_2$ or quantities proportional hereto at the relevant wavelengths. This determination principle is well known from the oxygen saturation meter OSM2 produced and sold by Radiometer A/S, Copenhagen, Denmark.

FIG. 19 shows the electronic circuit coupled to the optical unit shown in FIG. 17, which circuit in a simple way makes it possible to determine the modulation frequency providing a phase shift of 45° between excitation radiation and emission radiation.

A photodiode 501 is supplied from a voltage controlled oscillator 513 with a time modulated voltage signal. The photodiode 501 consequently emits time modulated radiation, which excites the luminophor in the luminophor containing PVC coating 5004. Subsequently the luminophor emits time modulated emission radiation, which is phase shifted in relation to the excitation radiation. The emission radiation falls onto the photodiode 507 emitting a time modulated current signal which is amplified with a constant quantity in an amplifier 509. The amplified signal is further amplified to a specified amplitude in an amplitude controlling unit 510. In a phase detector 511 the phase of signal from the unit 510 is compared to the phase of a reference signal, which is phase shifted 45° in relation to the time modulated voltage signal supplying the photodiode 501. The reference signal is generated in a unit 512. The phase detector 511 emits a signal controlling the voltage controlled oscillator 513. By means of the control signal the voltage controlled oscillator 513 is adjusted to such a frequency, that the emission radiation—and with this the input signal to the phase detector 511 from the unit 510—and the reference signal has the same phase. In other words, the voltage controlled oscillator 513 is adjusted to such a frequency that the emission radiation is phase shifted 45° in relation to the excitation radiation.

The frequency of the output signal from the voltage controlled oscillator 513 is registered and transformed to a digital quantity in the unit 516 and/or transformed in a frequency/analogue converter 514 to a signal registered by a printer or plotter 515.

In FIG. 19 the photometric system is for clearness represented only by the photodiodes 501 and 507. The other not shown components appear in FIG. 17.

With respect to the dimensions of the sample container used in the system according to the invention it is noted that each measuring chamber preferably has a volume of 1–50 µl, more preferably 5–25 µl and in particular 7–12 µl and that the distance between the opposed measuring chamber walls in the direction of the transmitted radiation is preferably 5–600 µm, more preferably 8–300 µm and in particular 10–200 µm.

Finally, it is noted that the radiation source and the radiation detector may comprise one component or several components. In the latter case each component preferably emits respectively detects radiation at a different wavelength than the other components. The several components of the radiation source may be provided as one integrated device or as separate devices. The same applies to the radiation detector.

We claim:

1. A method of photometric in vitro determination of at least one blood gas parameter in a sample of whole blood obtained directly from an in vivo locality comprising the steps of:

(a) connecting an at least partially transparent sample container to the in vivo locality to obtain a sample of whole blood, the sample container being open at one end to receive the sample of whole blood and being essentially sealed to the passage of liquids but permitting the venting of gas at the opposite end;

(b) transferring a sample of whole blood directly from the in vivo locality to the sample container;

(c) breaking the connection between the in vivo locality and the sample container;

(d) arranging the sample container relative to an optical system, wherein the optical system comprises a radiation source and a means for detecting radiation, such that the sample container is located between the radiation source and the radiation detection means;

(e) transmitting radiation from the radiation source to the sample;

(f) transmitting radiation emitted from the sample to the radiation detection means;

(g) detecting the radiation transmitted in step (f); and (h) determining the blood gas parameter of the sample of whole blood from the radiation detected in step (g).

2. The method of claim 1, wherein the sample container is placed in a sample container station and the sample container station is arranged relative to the optical system, such that the sample container is located between the radiation source and the radiation detection means of the optical system.

* * * * *